(12) United States Patent
Hofer et al.

(10) Patent No.: US 7,416,411 B2
(45) Date of Patent: Aug. 26, 2008

(54) MEDICAL HANDPIECE HAVING A CLAMPING SLEEVE FOR A TOOL

(75) Inventors: Bruno Hofer, Erlenmoos (DE); Uwe Mohn, Schelklingen (DE)

(73) Assignee: Kaltenbach & Voigt GmbH, Biberach (DE)

(*) Notice: Subject to any disclaimer, the term of this patent is extended or adjusted under 35 U.S.C. 154(b) by 153 days.

(21) Appl. No.: 11/038,568

(22) Filed: Jan. 18, 2005

(65) Prior Publication Data
US 2006/0024643 A1 Feb. 2, 2006

(30) Foreign Application Priority Data
Jul. 28, 2004 (DE) .................. 10 2004 036 454

(51) Int. Cl.
A61C 1/14 (2006.01)
B23B 5/22 (2006.01)
A61C 3/06 (2006.01)

(52) U.S. Cl. ............... 433/127; 279/23.1; 279/43.1; 279/46.1; 433/125

(58) Field of Classification Search ......... 433/125–127, 433/129; 279/23.1, 43.1, 46–54
See application file for complete search history.

(56) References Cited

U.S. PATENT DOCUMENTS 3,321,209 A * 5/1967 Sanders ............... 279/23.1
3,637,050 A * 1/1972 Hoffmeister ........... 433/132
3,672,060 A * 6/1972 Eibofner et al. ........ 433/127
4,281,988 A * 8/1981 Eibofner ............... 433/129
5,496,218 A 3/1996 Brahler ................ 464/182

FOREIGN PATENT DOCUMENTS

DE 29 23 358 12/1980

* cited by examiner

Primary Examiner—John J Wilson
(74) Attorney, Agent, or Firm—Marshall, Gerstein & Borun LLP

(57) ABSTRACT

A medical handpiece having an elongate grip part, in the forward end region of which a clamping sleeve is rotatably mounted, in which sleeve a shaft of a tool can be inserted and clamped, wherein the clamping sleeve has at least one axial clamping slot and in its longitudinal region a constriction section with a reduced inner cross-section and in the longitudinal region is surrounded by a sleeve receiving space. In order to improve the tool clamping the outer form of the clamping sleeve is, in the region of the constriction section, so configured that through the insertion of the shaft it forms a barrel-like outward bulge and in that the sleeve receiving space is in cross-section the same size or larger than the barrel-like output bulge.

15 Claims, 2 Drawing Sheets

MEDICAL HANDPIECE HAVING A CLAMPING SLEEVE FOR A TOOL

BACKGROUND OF THE DISCLOSURE

1. Field of the Disclosure

The disclosure relates to a medical, in particular a dental-medical, handpiece having an elongate grip with a sleeve for clamping a tool.

2. Related Technology

A handpiece of this kind is described in DE 29 23 358 C2. This known handpiece has a clamping sleeve, round in cross-section, which is rotationally fixed in a rotary bearing sleeve, wherein an inner space surrounded by the rotary bearing sleeve forms a sleeve receiving space for the clamping sleeve. The clamping sleeve has in a middle longitudinal region a constriction section and four slots taking in the entire wall thickness of the hollow cylindrical wall and distributed on the circumference, with which the clamping sleeve forms a so-called split chuck, into which a tool can be inserted and clamped with a shaft. The clamping sleeve thus forms a coupling, effective both in the axial direction and in the circumferential direction of the tool, for holding the tool shaft by means of elastically yielding clamping with the clamping webs present between the slots. The external circumference of the clamping sleeve is so strongly waisted in the region of the clamping webs that upon insertion of the tool shaft into the clamping sleeve the clamping webs can radially bend outwardly into the free space formed by the waist. Further, the rotary bearing sleeve and the clamping sleeve arranged therein can selectively be so mounted in the handpiece that their common middle axis extends longitudinally or transversely in the handpiece.

In U.S. Pat. No. 5,496,218 there is described a dental-medical handpiece having a tool attachment part which with its rear end region can be selectively placed on the forward end region of a grip sleeve, and pulled off again. The attachment part has at its free end a rotatably mounted polishing tool which stands in driving connection with a cylindrical drive pin coaxially rotatably mounted in the rearward end region of the attachment part. Upon placing of the tool attachment part, the drive pin is, with radially inwardly directed clamping tension, pushed into an inner longitudinally slotted clamping sleeve, which is formed by means of the forward end region of a drive shaft rotatably mounted coaxially in the grip sleeve. On the inner clamping sleeve there sits, likewise with radially inwardly directed clamping tension, a likewise longitudinally slotted outer sleeve which is surrounded by a free space of an axial bore in the grip sleeve receiving the drive shaft, so that upon insertion of the drive pin into the inner clamping sleeve both sleeves can expand radially.

With a handpiece of the kind concerned there is desired in particular in its forward end region a small cross-sectional size, in order to be able to use the handpiece also in body cavities of patients, e.g. in the mouth, while ensuring an adequate view of the treatment site. Further, a sufficiently large clamping force for clamping the tool shaft is necessary in order to ensure, in functional operation, that the tool is carried along in rotation.

GENERAL DESCRIPTION

The disclosure provides a handpiece of the general type described above, with improved tool clamping, in particular with strengthened clamping. This may be achieved without a substantial increase of the cross-sectional dimension of the handpiece. Moreover, the disclosure provides improvement while ensuring a simple and economically producible construction and ensuring a reliable mounting function.

According to the disclosure, the clamping force at the clamping sleeve utilizes the stability of the clamping webs; with increasing stability of the clamping webs the clamping force increases.

With a configuration in accordance with the disclosure, the outer form of the clamping sleeve in the region of the constriction section is so configured that through the insertion of the tool shaft a barrel-like outward bulge forms, and the inner cross-section of the sleeve receiving space is the same or larger than the outer cross-section of the barrel-like outward bulge. Through this, the free space necessary for the spreading of the clamping web(s) is not restricted by the cross-section of the clamping sleeve but there is available a free space which is greater than the cross-section of the clamping sleeve and into which the clamping web(s) can be bent outwardly. Consequently, the waisting of the clamping sleeve can be slighter than is necessary for the outward bending of the clamping web(s). This in turn makes it possible to form the clamping web(s) with a greater radial thickness, through which the web(s) is (are) stabilized and strengthened and can exercise a greater clamping force upon outward bending, due to a greater resistance moment. This stabilization or strengthening of the clamping web(s) can be achieved without requiring a cross-sectional enlargement of the handpiece or of the grip sleeve. This is possible because the sleeve receiving space can be dimensioned greater than the sleeve cross-section axially neighboring the outward barrel-like bulging.

The configuration in accordance with the disclosure is suitable in particular for a handpiece in which the clamping sleeve is arranged with its longitudinal axis in the longitudinal direction of the handpiece. With such a handpiece no rotary bearing sleeve surrounding the clamping sleeve, which receives the clamping sleeve is needed; rather, the clamping sleeve may be a forward end region of a drive shaft extending longitudinally in the handpiece, which drive shaft is rotatably mounted in the handpiece. Further, the omission of the rotary bearing sleeve makes it possible to form the handpiece with a small cross-sectional size.

Further, stabilization of one clamping web(s) is promoted if this ends without a widening, e.g. as a parallel slot. Such a slot form can be produced in simple and economically manufacturable manner by means of milling applied from the outside, in particular by means of a disk milling cutter.

In particular for a handpiece for a speed of rotation above $1000 \text{ m}^{-1}$, and in particular for a high speed handpiece, it is advantageous to arrange a plurality of preferably uniformly distributed clamping webs on the circumference, or to apply corresponding slots, which form the clamping webs. This leads to better exploitation of the material tension and to a concentric positioning of the tool shaft in the mounted condition. It has proved to be particularly advantageous when three slots or clamping webs are present, which are uniformly distributed on the circumference.

Further disclosed developments make possible a simple and economic manufacture and a small, well functioning construction.

The configuration in accordance with the disclosure is suitable in particular for a compressed air drive in the handpiece, which e.g. may be constituted by means of a turbine and with which a high speed of rotation can be attained.

BRIEF DESCRIPTION OF THE DRAWINGS

Advantageous configurations of the disclosed device will be described in more detail with reference to preferred embodiments and the drawings. There is shown.

DETAILED DESCRIPTION OF PREFERRED EMBODIMENTS

Figure 1:
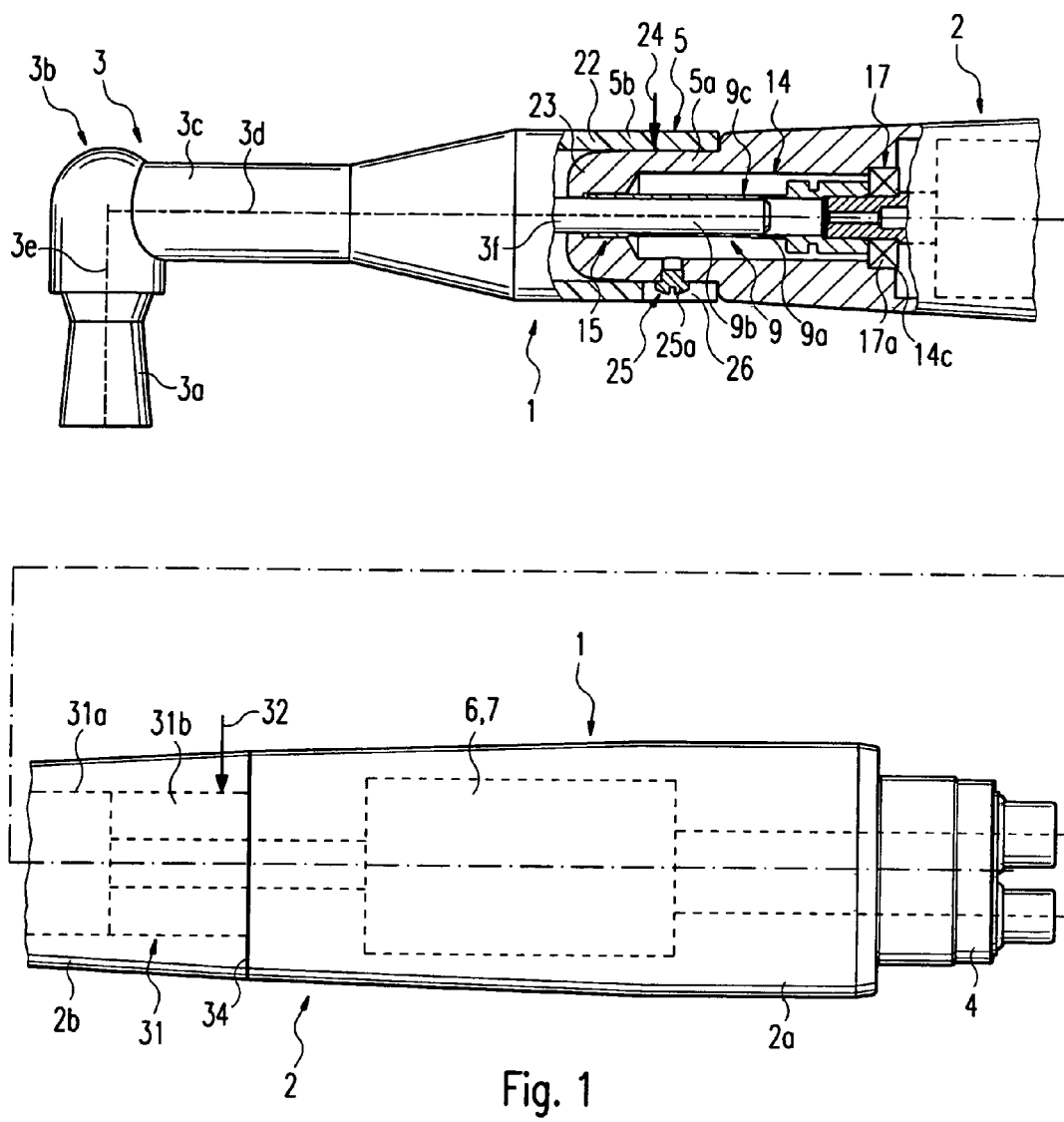
FIG. 1 shows a medical, in particular medical-dental hand instrument having a handpiece and a tool which can be connected therewith, in a side view, partly axially sectioned.
Figure 2:
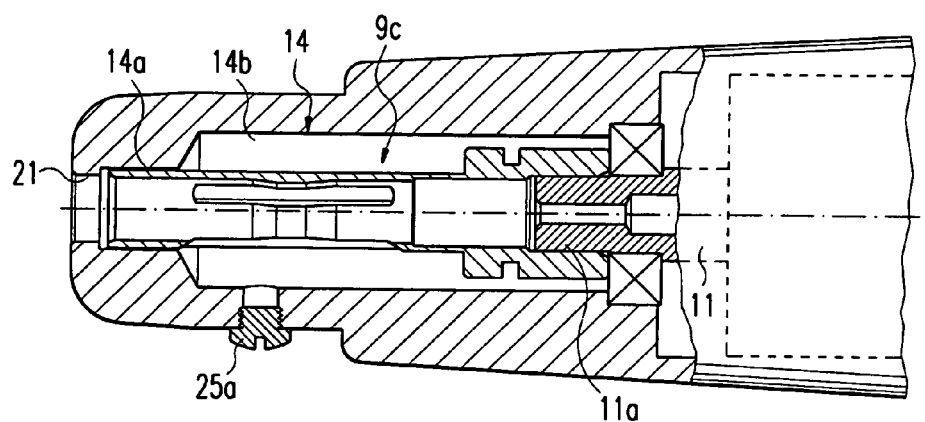
FIG. 2 shows the sectioned region of the handpiece in a representation to an enlarged scale.

The main parts of the hand instrument, generally designated 1, are a handpiece 2 in the form of an elongate or rod-shaped grip part, a tool 3, a coupling element 4, arranged at the rearward end of the handpiece 2, which is part of a connection coupling for connecting the handpiece 2 with a supply line (not shown), a forward coupling device 5 having a coupling element 5a arranged at the forward end of the handpiece 2 and a coupling element 5b arranged at the rearward end of the tool, for releasable connection of the tool 3 with the handpiece 2, a rotary drive 6 having a rotary motor 7 in the handpiece, a drive coupling 9 having a drive coupling element 9a arranged in the forward end region of the handpiece 2 and a drive coupling element 9b arranged at the tool 3, which is drivingly connected with a working element 3a of the tool 3.

In the case of the exemplary embodiment, the tool 3 is formed by means of a straight (not shown) or angled tool attachment part, generally designated 3b, which has a tube-like housing 3c from the forward end region of which the working element 3a extends, preferably to the side. The working element 3a is preferably a rotatably mounted polishing element, which stands in driving connection with the drive coupling element 9b, in the case of a straight tool 3 by means of one drive shaft section (not shown) or in the case of an angled tool 3, as in the present case, by means of two drive shaft sections 3d, 3e indicated in outline.

In the case of the exemplary embodiment, the drive coupling 9 is a plug-in clamping coupling having a drive coupling element 9a on the handpiece side in the form of a clamping sleeve 9c, into which the drive coupling element 9b on the tool side, in the form of a drive shaft 3f, can be inserted and elastically clamped upon connection of the tool 3. The drive shaft 3f can project rearwardly beyond the coupling element 5b.

Figure 3:
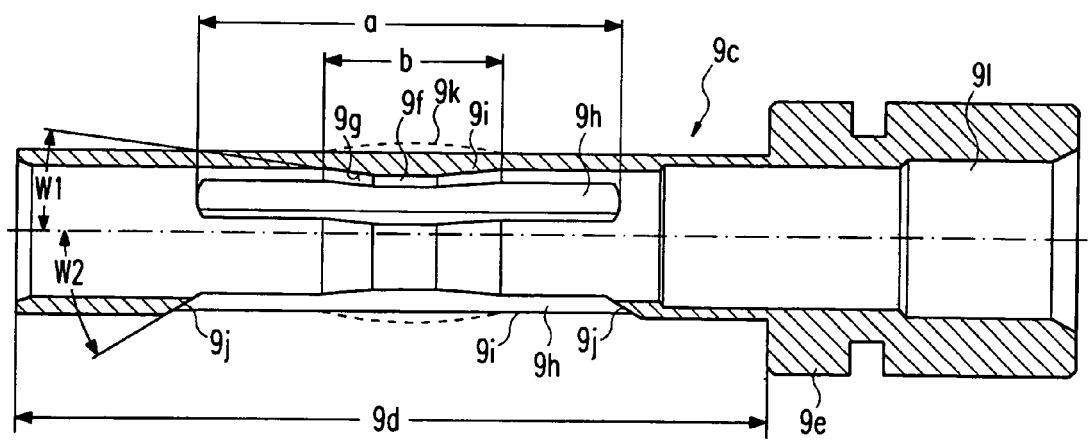
FIG. 3 shows a clamping sleeve of the handpiece as an individual part, in axial section and in a representation to an enlarged scale.

As can be understood in particular from FIG. 3, the clamping sleeve 9c has a forwardly extending sleeve section 9d which at least externally has a cylindrical form, to which there adjoins, preferably in one piece, rearwardly a thickened hub 9e which likewise may have a hollow cylindrical form. The clamping sleeve 9c has in the middle region of the sleeve section 9d, inwardly, a constriction section 9f with an introduction surface 9g at its end away from the rotary drive 6. The introduction surface 9g may be a rounded or oblique surface e.g. a taper surface, which includes with the middle axis of the clamping sleeve 9c an acute angle W1, which is preferably smaller than about 6°.

In the region of the constriction section 9f, the clamping sleeve 9c is axially slotted, so that at least one circumferential section of the clamping sleeve 9c can spring radially outwardly. In the case of the exemplary embodiment there are provided three slots 9h distributed approximately uniformly on the circumference, the length a of which slots is greater than the length b of the constriction section 9f, whereby the slots 9h axially project beyond the constriction section 9f with both their ends. Between the slots 9h there are located clamping webs 9i which are connected in one piece with the remaining tube sections of the clamping sleeve section 9d. At their ends, the slots 9h are bounded by oblique or rounded end surfaces 9j which develop radially outwardly divergently and include with the middle axis of the clamping sleeve 9c an acute angle W2 of e.g. about 15° to 30°. The slots 9h are preferably worked in by material removal, e.g. with a non-illustrated disk milling cutter, which can be sunk into the sleeve wall radially and in its diameter is so large that its circumferential surface forms the end surfaces 9j.

The inner cross-sectional size of the sleeve section 9d is, taking into account a slight play for movement, adapted to the outer cross-sectional size of the drive shaft 3f. The inner cross-sectional size of the constriction section 9f is, in contrast, smaller than the cross-sectional size of the shaft 3f. Upon closure of the coupling device 5, i.e. upon insertion of the drive shaft 3f into the clamping sleeve 9c, the clamping webs 9i bend elastically radially outwardly, whereby they form an outward bulge 9k projecting radially from the cylindrical outer form of the sleeve section 9d, which bulge is located in the region of the constriction section 9f.

The clamping sleeve 9c is fixed for rotation with the forward end region of a drive shaft 11 rotatably mounted coaxially in the handpiece 2, which drive shaft in the case of the exemplary embodiment is formed by means of a drive shaft pin 11a. The clamping sleeve 9c is located in a sleeve receiving space 14 of the handpiece 2 which at least in the slotted axial region a of the clamping sleeve 9c is in cross-section the same or larger than the outward bulge 9k of the clamping webs 9i formed by means of the slots 9h. Upon insertion of the tool 3 with its shaft into the clamping sleeve 9c, the clamping webs 9i can thus bend elastically outwardly and form the bulge 9k.

In the case of the exemplary embodiment, the sleeve receiving space 14 comprises a plurality of axial space stages of different sizes in cross-section. A forwardmost receiving space stage 14a has a hollow cylindrical cross-sectional form, and with its inner surface forms a rotary mounting 15 for the forward end section of the clamping sleeve 9c, the forward end region of which is cylindrical and formed with a cross-sectional size which, with a play for sliding, fits into the forwardmost receiving space stage 14a. In the region of the forward ends of the clamping webs 9i or before the forward ends of the clamping webs 9i, the sleeve receiving space 14 is broadened to a second receiving space stage 14b the cross-section of which is the same (not illustrated) or greater than the outward bulge 9k. In the region of the clamping webs 9i, the clamping sleeve 9c is thus surrounded by the free space of the second receiving space stage 14b. The second receiving space stage 14b may be formed by means of a hollow cylindrical bore, which rearwardly opens out into a drive receiving space, which is enlarged in cross-section and accommodates the drive 6 and/or a transmission 7, which is e.g. cylindrically formed and sits appropriately in the inner peripheral wall of the drive receiving space, whereby it may be arranged before the rotary motor 7, for example likewise arranged in the drive receiving space.

For stabilizing the drive it is advantageous to mount the drive shaft pin 11a rotatably in a rotary bearing 17, which in the case of the exemplary embodiment is a roller bearing 17a which sits with its inner ring on the drive pin 11a and with its outer ring sits in the second receiving space stage 14b or in a likewise enlarged cylindrical bearing stage 14c.

The clamping sleeve 9c sits in its rearward end region with a hollow cylindrical wall 91 on the forward end region of the drive pin 11a, and it is rigidly attached thereon, e.g. by press fitting. The longitudinal section of the drive pin 11a carrying the clamping sleeve 9c is, in cross-section, preferably slightly smaller dimensioned than its longitudinal section accommodating the rotary bearing 17. Through this, the installation of the rotary bearing 17 is simplified, because the inner ring of the rotary bearing 17 can be pushed over the forward longitudinal section of the drive pin 11a with play for movement and must only be purposively pushed on to the second drive shaft pin section.

The handpiece 2 has at its forward end a coaxial insertion opening 21 for the shaft 3f of the tool 3, the cross-sectional size of which may be somewhat smaller than the cross-sectional size of the first receiving space stage 14a.

The clamping webs 9i are segment-like parts of the sleeve section 9d which, in the relaxed rest disposition of the clamping webs 9i, is preferably externally cylindrical. The clamping webs 9i are thus relatively stable and in the bent out condition exercise a sufficiently great radially inwardly directed elastic clamping force on the shaft 3f.

In the case of the present exemplary embodiment, the tool 3 is a so-called tool attachment part 3b which with a insertion sleeve 22, arranged in its rearward end region and formed by means of the wall of the tube shape, can be inserted on to a forward insertion pin 23 forming the coupling element 5a and can be secured against an unintended release by means of a radially inwardly effective securing element 24. The securing element 24 can for example be formed in that the ring-shaped wall of the insertion sleeve 22 sits on the insertion pin 23 with a radial clamping tension which is so great that the tool attachment part 3b can radially inserted on, and again removed, but which is also so great that during the operation of the hand instrument 1 the tool attachment part 3b does not unintentionally release.

For rotary positioning of the tool attachment part 3b on the handpiece 2 there can be provided a rotary securing means 25 which in the case of the exemplary embodiment is formed by means of a securing screw 25a which is radially screwed into the insertion pin 23 and thus with its screw head stands out from the insertion pin 23 and sits in a slot 26 in the insertion sleeve 22. The section 26 is opened to the rear so that the screw head can be introduced therein upon putting the tool attachment part 3b in place.

The tool 3 is preferably a so-called disposable tool that after one use in treatment of the patient is not used again and is disposed of. Thus no cleaning or disinfection or sterilization of the tool 3 is required. It may also, however, be a multiple-use tool, that is used on patients repeatedly and thus should be disinfected or sterilized after use. In the case of the exemplary embodiment, at least the insertion sleeve 22, preferably also the housing 3c or the tool 3, is formed of a plastic material. These parts may, however, also be of corrosion resistance metal, in particular stainless steel.

In the case of the present exemplary embodiment, the handpiece 2 is of a rearward and a forward handpiece part 2a, 2b which are releasably connected with one another by means of an axially effective plug-in coupling 31. The plug-in coupling 31 may be formed by means of a plug-in recess 31a in the one handpiece part 2b and a plug-in pin 31b on the other handpiece part 2a, which can be inserted therein, which in the assembled condition can be arrested by means of an arresting device 32, in order to prevent an unintended release of the plug-in 31.

In the case of the exemplary embodiment, the separating joint, extending transversely, between these parts 2a, 2b is designated by 33. The plug-in pin 31b may project forwardly from the rearward handpiece part 2a, preferably coaxially, whereby the forward handpiece part 2b has the plug-in recess 31a.

The plug-in coupling 31 may be so formed that it does not constitute a quick-fastening connection and thus the handpiece 2 can be divided into the two handpiece parts 2a, 2b in a medical practice and/or only in a workshop. Such a separability serves primarily for the assembly or disassembly of the handpiece 2 in a workshop.

For reasons of handling it is particularly advantageous to configure the plug-in coupling 31 such that the rearward or forward handpiece parts 2a, 2b are freely rotatably mounted on one another, whereby the plug-in pin 31a and the plug-in recess 31b may form a rotary bearing. With such a configuration, the forward handpiece part 2b can be easily and radially rotated with the operating hand, whereby the rearward handpiece part 2b can remain in its position. Such a plug-in coupling is per se known and in the field is designated a plug-in/turn coupling.

The invention claimed is:

1. Medical handpiece having an elongate grip part, having a forward end region, and a clamping sleeve in which a shaft of a tool can be inserted and clamped being rotatably mounted in said forward end region of said grip part, wherein the clamping sleeve has a longitudinal region with a constriction section having an increased inner thickness compared to a remainder of said longitudinal region, said increased thickness resulting in a reduced inner cross-section in said constriction section, and a plurality of axial clamping slots extending longitudinally along a portion of the clamping sleeve including said constriction section, wherein one or more portions of said clamping sleeve between said plurality of axial clamping slots define one or more clamping webs, said clamping sleeve being surrounded by a sleeve receiving space including a forwardmost receiving space stage and a second receiving space stage, wherein an inner surface of said forwardmost receiving space stage includes a rotary mounting for a forward end section of said clamping sleeve, wherein, without the insertion of said tool shaft, an outer form of said clamping sleeve is cylindrical in the region of the constriction section, and is so configured that an outer diameter of said longitudinal region is substantially equal along the entire length of said longitudinal region and, with the insertion of the tool shaft, the outer form of said one or more clamping webs is outwardly convex relative to said clamping sleeve cylindrical form, said one or more clamping webs having a barrel-like outward bulge, wherein said sleeve receiving space is broadened from the forwardmost receiving space stage to the second receiving space stage in the region of said clamping webs, the cross section of said second receiving space stage being the same or greater than said barrel-like outward bulge.

2. Handpiece of claim 1, wherein each of said one or more clamping webs has relaxed and bent conditions, wherein said bent condition of said one or more clamping webs exerts a radially inwardly directed elastic clamping force on said tool shaft.

3. Handpiece of claim 1, wherein the clamping sleeve extends in a longitudinal direction of the grip part.

4. Handpiece of claim 1, wherein the clamping sleeve sits with a rearward end region thereof rotationally fixed on a drive shaft.

5. Handpiece of claim 4, wherein the clamping sleeve sits on the drive shaft with a radial clamping tension.

6. Handpiece of claim 1, wherein the clamping sleeve extends into the grip part from the rear of the grip part.

7. Handpiece of claim 1, wherein the clamping sleeve is radially supported in a forward end region thereof.

8. Handpiece of claim 7, wherein the clamping sleeve is rotatably mounted in its forward end region.

9. Handpiece of claim 7, wherein the tool attachment part has at a forward end thereof a working element which stands out from the tool body.

10. Handpiece of claim 9, wherein the working element is rotatable.

11. Handpiece of claim 9, wherein the working element stands out to a side of the tool body.

12. Handpiece of claim 7, wherein at least the insertion sleeve comprises a plastic material.

13. Handpiece of claim 1, wherein the tool is a tool attachment part having a rearward insertion sleeve with which it can be inserted on to a forward insertion pin on the handpiece and can thereby be positioned.

14. Handpiece of claim 1, wherein the tool is a disposable tool.

15. Handpiece of claim 1, wherein the sleeve receiving space is in cross-section larger than the barrel-like outward bulge.

* * * * *